US00PP13437P2

(12) United States Plant Patent
Heims

(10) Patent No.: US PP13,437 P2
(45) Date of Patent: Dec. 31, 2002

(54) TIARELLA PLANT NAMED 'JEEPERS CREEPERS'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/894,589

(22) Filed: Jun. 28, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Tiarella plant characterized by its unique creeping habit with good vigor, fine leaf form and coloration, and showy white flowers.

2 Drawing Sheets

The present invention relates to a new and distinct hybrid of Tiarella, of the family Saxifragaceae, which originated from a cross between unknown parents. This new Tiarella was one of many seedlings grown from select plants that were mass pollinated in the greenhouse in Canby, Oreg. Due to the fact that there were several different species involved, no species designations are given.

What makes this plant unique is its slow creeping habit. Tiarella normally is either clumping or running to five or more feet a year. Tiarella 'Jeepers Creepers' spreads 4 to 12 inches a year. It also has good quality foliage, vigor, and good flower size and number of flowers.

The new variety has been reproduced only by asexual propagation (division and tissue culture). Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
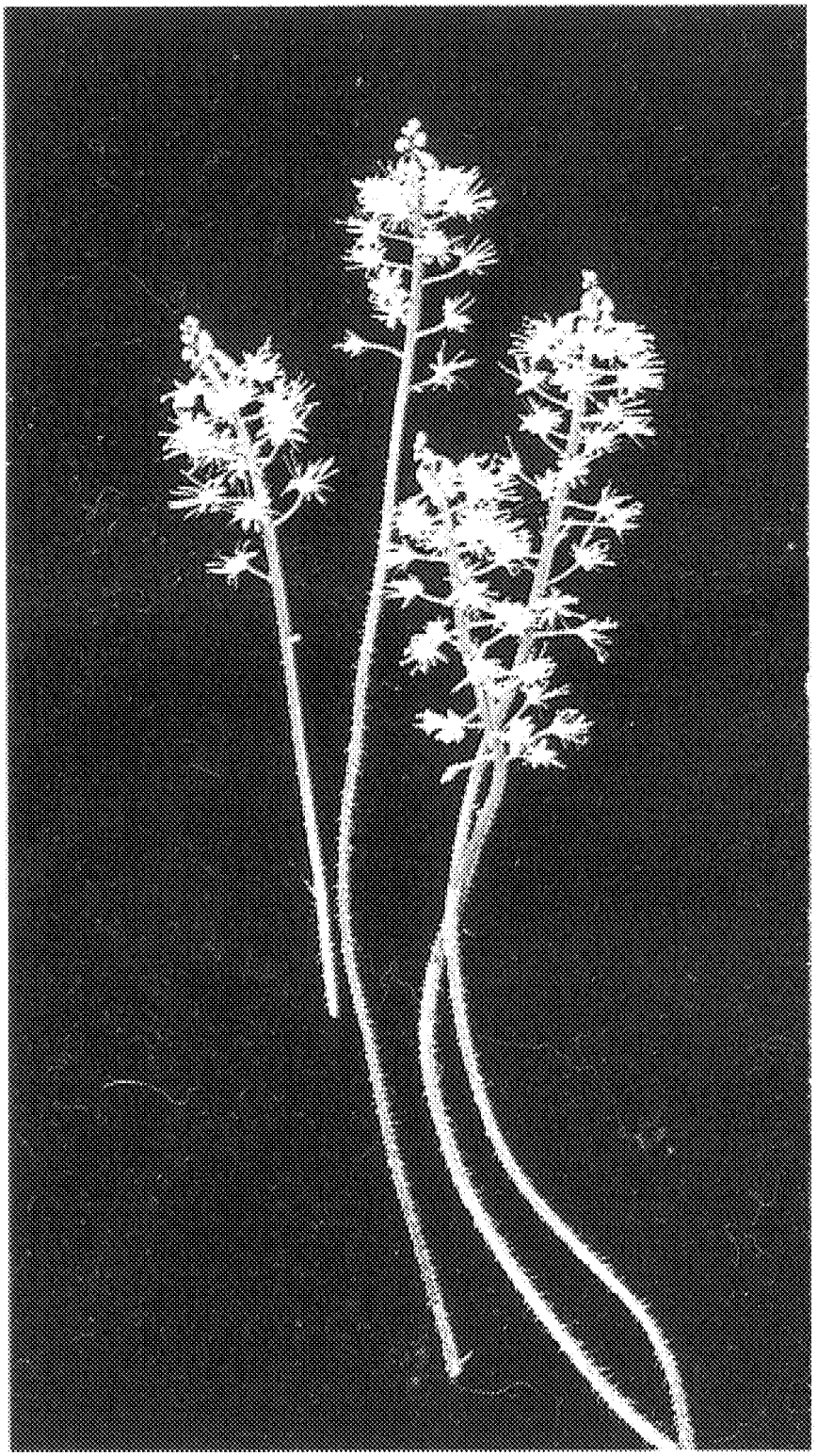
FIG. 1 shows the late spring flowers of the new plant.
Figure 2:
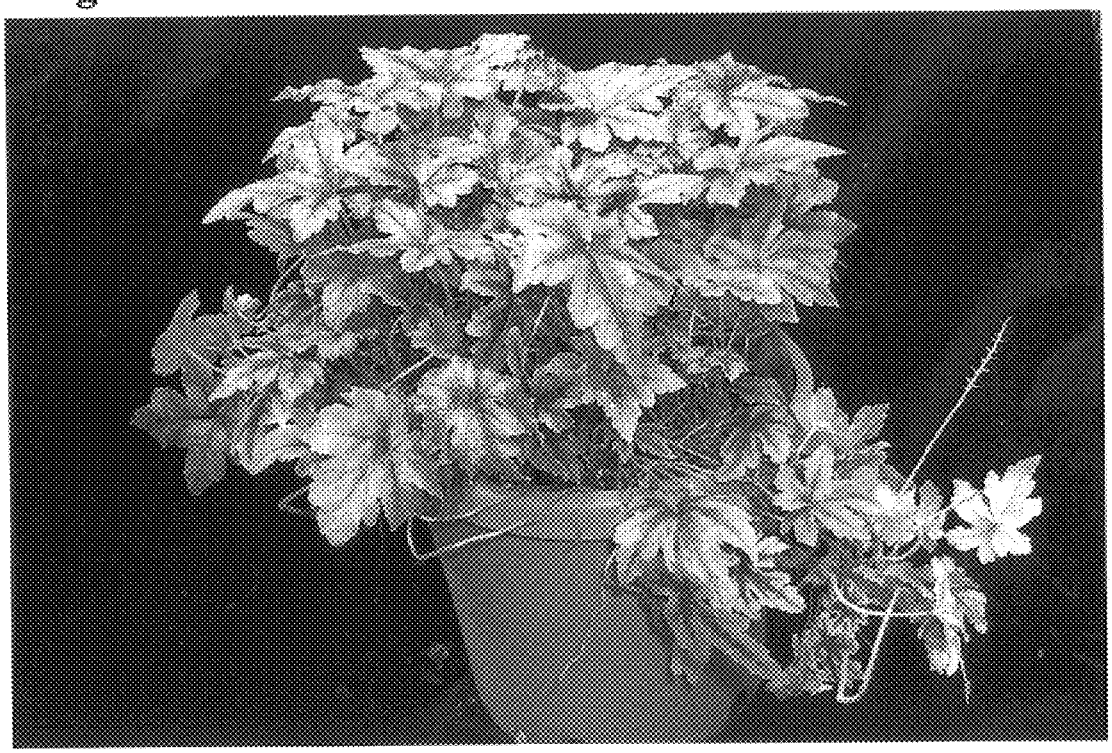
FIG. 2 shows the plant in a two gallon pot.

The following is a detailed description of the new Tiarella hybrid based on observations of one and a half year old specimens grown in two gallon pots in a cool greenhouse in Canby, Oreg. The color descriptions are all based on The Royal Horticultural Society Colour Chart.

Botanical classification: Tiarella hybrid.
Cultivar name: 'Jeepers Creepers'.
Plant:
- *Form.*—Rhizomatous, herbaceous perennial.
- *Hardiness.*—USDA Zone 4 to 9.
- *Size.*—18 cm tall and 31 cm wide in Canby, Oreg.

Leaf:
- *Type.*—Simple.
- *Arrangement.*—Alternate, when visible on old stems.
- *Shape.*—Ovate.

- *Lobing/division.*—Variable, 3 to 5 lobes, palmately parted, with the terminal lobe the longest, parted from ½ to ⅔ of leaf.
- *Venation.*—Palmate, with dark coloration following veins.
- *Margins.*—Irregulary crenate, leaves often cup back slightly.
- *Apex.*—Variable, from obtuse to acute to mucronulate.
- *Base.*—Cordate, sometimes overlapping.
- *Size.*—10 cm long and 9.2 cm wide.
- *Texture.*—Rough. Hirsute top and bottom with the bottom hairs shorter.
- *Petiole length.*—12 cm. at the longest.
- *Petiole texture.*—Strongly pubescent.
- *Petiole color.*—Closest to Greyed Orange 177A but with more purple.
- *Leaf color.*—Variable. Normally Green RHS 137B with dark maroon in leaf center and along veins. Greyed Purple 187A. In the spring the new growth is Green 144A. The winter colors are Greyed Orange 174D to 176A.
- *Abaxial.*—Yellow Green 146B.

Inflorescence:
- *Type.*—Panicle.
- *Number of flowers.*—Approximately 50 per panicle.
- *Peduncle.*—With one to two green cauline leaves and one to three branches. Height — 30 to 50 cm. Diameter — 0.25 to 0.30 cm. Color — Yellow Green 152A. Texture — Hispid.
- *Pedicel.*—Length — 0.8 cm. Texture — Puberulent. Color — Greyed Purple 183B to lighter greyed purple over yellow green.
- *Bloom period.*—April to May in Canby, Oreg.

Flower bud:
- *Size.*—0.3 to 0.4 cm.
- *Description.*—Puberulent, downfacing, campanulate when opening.
- *Color.*—Creamy white. Yellow White 158A.

Flower:
- *Type.*—Perfect, actinormorphic, sepals petaloid.
- *Shape.*—Rotate.
- *Size.*—0.95 cm wide.
- *Color.*—White 155D sepals and petals.
- *Petal count.*—5.
- *Petal shape.*—Elliptic with a clawed base.
- *Petal size.*—0.5 cm long and 0.2 cm wide.
- *Sepal type.*—Petaloid, divided almost to the base.

*Sepal size.*—⅔ the size of the petals.
*Stamen number.*—10, conspicuously exerted.
*Pistil.*—White 155D.
*Pollen.*—Greyed Orange 170B.
*Anthers undehisced.*—Red Orange 31B.
*Filaments.*—White 155D.
*Fragrance.*—None.
*Lastingness.*—A spike blooms for about 3 weeks and may branch extending the bloom time.

Fruit:
*Type.*—A one celled, horned capsule.
*Fertility.*—Fertile.
*Color.*—Tan. Grey-Brown 199D.

Seed:
*Shape.*—Elliptic.
*Size.*—Less than 1 mm.
*Color.*—Black 202A.

Disease tolerance: Excellent disease resistance to powdery mildew, the common problem of Tiarellas.

COMPARISON TO OTHER PLANTS

Tiarella 'Jeepers Creepers' is unique from other Tiarella in having a creeping habit rather than running or clumping habit. This character, along with good vigor, foliage, and flowers made the instant plant stand out from all others. The breeder knows of no other Tiarella plant with all these characteristics.

I claim:

1. A new and distinct hybrid of Tiarella plant substantially as shown and described, characterized by a slow creeping habit and good vigor, foliage, form and flowers.

* * * * *